(12) United States Patent  
Minnich et al.

(10) Patent No.: US 7,264,937 B2
(45) Date of Patent: Sep. 4, 2007

(54) OXYDECAHYDRONAPHTHALENE MODULATORS OF HM74

(75) Inventors: Anne Minnich, Flemington, NJ (US); Theresa Kuntzweiler, Bernardville, NJ (US); Haifeng Eishingdrelo, Montville, NJ (US); Michael Angelastro, Bridgewater, NJ (US); Stephan Henke, Tucson, AZ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 11/057,263

(22) Filed: Feb. 14, 2005

(65) Prior Publication Data

US 2005/0187263 A1   Aug. 25, 2005

Related U.S. Application Data

(60) Provisional application No. 60/546,012, filed on Feb. 20, 2004.

(51) Int. Cl.
*G01N 33/53* (2006.01)
(52) U.S. Cl. ...................................................... 435/7.1
(58) Field of Classification Search ..................... None
See application file for complete search history.

(56) References Cited

U.S. PATENT DOCUMENTS 4,522,811 A   6/1985   Eppstein et al.

6,399,653 B1   6/2002   Henke

FOREIGN PATENT DOCUMENTS

WO   WO0022129   4/2000

OTHER PUBLICATIONS

E. Von Roedern, A new method for the characterization of chemical libraries—solely by HPLC retention times, Molecular Diversity, vol. 3, 1998, pp. 253-256.
Nomura et al., Molecular cloning of cDNAs encoding a LD78 receptor and putative leukocyte chemotactic peptide receptors, Internatinal Immunology, vol. 5, No. 10, 1993, pp. 1239-1249.
Wise et al., Molecular Identification of High and Low Affinity Receptors for Nicotinic Acid, J. of Biological Chemistry, vol. 278, No. 11, Mar. 14, 2003, pp. 9869-9874.

*Primary Examiner*—Ralph Gitomer
*Assistant Examiner*—Bin Shen

(57) ABSTRACT

Host cells expressing HM74 were used to obtain oxydecalin-like molecules with agonist activity having the following structure:

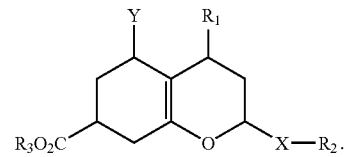

3 Claims, No Drawings

OXYDECAHYDRONAPHTHALENE MODULATORS OF HM74

BACKGROUND OF THE INVENTION

The G protein-coupled receptors (GPCRs) are integral membrane proteins that are involved in cellular signal transduction. GPCRs respond to a variety of extracellular signals, including neurotransmitters, hormones, odorants and light, and are capable of transducing signals so as to initiate a second messenger response within the cell. Many therapeutic drugs target GPCRs because those receptors mediate a wide variety of physiological responses, including inflammation, vasodilation, heart rate, bronchodilation, endocrine secretion and peristalsis.

Diseases such as asthma, chronic obstructive pulmonary disease (COPD), psoriasis, and rheumatoid arthritis (RA) generally are considered to have an inflammatory etiology involving T helper cells, monocyte-macrophages and eosinophils. Current anti-inflammatory therapy with corticosteroids is effective in asthma but is associated with metabolic and endocrine side effects. The same is possibly true for inhaled formulations that can be absorbed through lung or nasal mucosa. Satisfactory oral therapies for RA or COPD currently are lacking.

Molecular cloning of HM74 from human monocytes predicted HM74 to be a chemokine receptor (Nomura et al., Int. Immunol. (1993) 5(10):1239-1249). HM74 is expressed primarily in bone marrow, spleen, tonsil and trachea.

Human cells also contain a related but distinct receptor, HM74A. The amino acid sequences of HM74 and HM74A are about 95% identical. However, the ligand of HM74A is known whereas the ligand of HM74 is unknown. Niacin or nicotinic acid is the HM74A ligand, Wise et al., J. Biol. Chem. 278:9869-9874, 2003. Niacin is but a poor activator of HM74.

The mouse genome contains an HM74A gene but not an HM74 gene.

Under certain circumstances, HM74 and HM74A demonstrate coregulation. Using Taqman-PCR, applicants found that HM74 and HM74A expression is induced 50-fold by TNFα in granulocytes and 10-20-fold by LPS or TNFα in monocytes. HM74 and HM74 expression also are induced 4-5-fold in normal human bronchial epithelial cells with the TH2 cytokines, IL-4 or IL-13, known to be important in the etiology of asthma. HM74 and HM74A expression are upregulated in human primary eosinophils by IL-5. Finally, pulmonary HM74A expression is upregulated in a murine experimental asthma model.

The restricted tissue distribution of HM74 and HM74A, and the regulation thereof suggest a role for HM74 and HM74A in inflammatory processes, such as asthma, COPD and RA.

Given the role GPCRs have in disease and the ability to treat diseases by modulating the activity of GPCRs, identification and characterization of GPCR ligands can provide for the development of new compositions and methods for treating disease states that involve the activity of a GPCR. The instant invention identifies and characterizes molecules that engage HM74, and provides compositions and methods for applying the discovery to the identification and treatment of related diseases.

SUMMARY OF THE INVENTION

The instant invention relates to molecules that activate HM74 but not HM74A.

In another aspect of the invention, methods are disclosed for identifying modulators of HM74. For example, a method of interest comprises the steps of providing a chemical moiety, providing a cell expressing HM74 and determining whether the chemical moiety modulates the signaling activity of HM74, including whether such modulation occurs in the presence or absence of an agonist of the instant invention. In a related aspect, the chemical moieties can include, but are not limited to, peptides, antibodies, agonists, inverse agonists and antagonists. Alternatively, a known modulator can be used in a competition assay to identify other modulators.

Fused ring dihydropyrans (also known as oxydecahydronaphthalene and oxydecalin) activate HM74. Those compounds cause selective dose-responsive calcium mobilization in cells expressing HM74, such as CHO cells, 293 cells and L1.2 cells.

The oxydecalins of interest have the following structure:

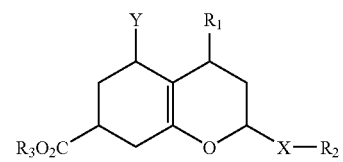

where X is O, $NR_2$ or S;

$R_1$ is a $C_1$-$C_{18}$ alkyl, which may be branched, may contain a heteroatom or may be substituted, or combinations thereof; a $C_1$-$C_{18}$ alkenyl, which may be branched, may contain a heteroatom or may be substituted, or combinations thereof; a $C_1$-$C_{18}$ alkynl, which may be branched, may contain a heteroatom or may be substituted, or combinations thereof; a $C_3$-$C_{18}$ aryl which may contain a side group, may contain a bridge, may contain a heteroatom or may be substituted, or combinations thereof; or a $C_5$-$C_{18}$ cycloalkyl which may contain a side group, may contain a bridge, may contain a heteroatom or may be substituted, or combinations thereof; or combinations thereof;

R2 is an R1 group; or R2 can be a (C1-C10) alkyl-(C3-C10) cycloalkyl, which may be branched, may contain a heteroatom or may be substituted, or combinations thereof; or X and R2 may form a ring;

R3 is H or R1; and

Y is carbonyl, a Schiff base, an oxine, a ketal, an acetal, an oxazolidine, a thiazolidine or an enol ester.

The compounds of interest generally are agonists. Thus, a compound of interest could be developed as a drug candidate. A compound of interest also could be used to identify other molecules that modulate HM74 by, for example, competition assays.

Another aspect of the invention includes therapeutic compositions, where such compositions include nucleic acids, antibodies, polypeptides, agonists, inverse agonists and antagonists. Further, methods of the invention also include methods of treating disease states and modulating HM74 signaling activity by administering such therapeutic compositions to a patient in need thereof.

Those and other aspects of the invention will become evident on reference to the following detailed description and attached drawings. In addition, various references are set forth below that describe in more detail certain procedures or compositions. Each of the references hereby is incorporated herein by reference as if each were individually noted for incorporation.

DETAILED DESCRIPTION OF THE INVENTION

The instant invention is based on the discovery of molecules that activate HM74.

The HM74 coding sequence is known, Nomura et al., supra. Methods for obtaining, making and using HM74 are provided herein. Changes to the HM74 coding sequence and amino acid are tolerated so long as the known functional activities of HM74 are not impacted adversely.

The instant compounds modulate HM74, are agonists of HM74, and thus are drug candidates for disorders characterized by inflammation, such as asthma.

The instant compounds also can be used to screen for HM74 antagonists. For example, cells expressing HM74 are exposed to a test compound and then to an agonist of the instant invention. Then the effect of the test compound on, for example, calcium mobilization, can be ascertained to determine whether the test compound reduces the calcium mobilization levels induced by the agonist of the instant invention.

Other such assays to identify, for example, agonists and inverse agonists, are contemplated to fall within the scope of the instant invention.

The oxydecalins of interest have the following structure:

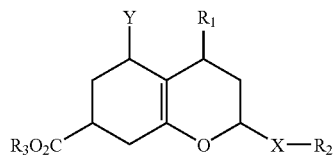

where X is O, $NR_2$ or S;

$R_1$ is a $C_1$-$C_{18}$ alkyl, which may be branched, may contain a heteroatom or may be substituted, or combinations thereof; a $C_1$-$C_{18}$ alkenyl, which may be branched, may contain a heteroatom or may be substituted, or combinations thereof; a $C_1$-$C_{18}$ alkynl, which may be branched, may contain a heteroatom or may be substituted, or combinations thereof; a $C_3$-$C_{18}$ aryl which may contain a side group, may contain a bridge, may contain a heteroatom or may be substituted, or combinations thereof; or a $C_5$-$C_{18}$ cycloalkyl which may contain a side group, may contain a bridge, may contain a heteroatom or may be substituted, or combinations thereof; or combinations thereof;

$R_2$ is an $R_1$ group; or $R_2$ can be a ($C_1$-$C_{10}$) alkyl-($C_3$-$C_{10}$) cycloalkyl, which may be branched, may contain a heteroatom or may be substituted, or combinations thereof; or X and $R_2$ may form a ring;

$R_3$ is H or $R_1$; and

Y is carbonyl, a Schiff base, an oxine, a ketal, an acetal, an oxazolidine, a thiazolidine or an enol ester.

The compounds of interest generally are agonists. Thus, a compound of interest could be developed as a drug candidate. A compound of interest also could be used to identify other molecules that modulate HM74 by, for example, competition assays.

The term "alkyl" means a straight or branched chain hydrocarbon. Representative examples are methyl, ethyl, propyl, isopropyl, butyl, isobutyl, tert-butyl, sec-butyl, pentyl and hexyl. The hydrocarbon can contain one or more unsaturated triple bonds.

The term "alkoxy" means an alkyl group bound to an oxygen atom. Examples are methoxy, ethoxy, propoxy, butoxy and pentoxy.

"Aryl" is a ring which is an aromatic hydrocarbon. Examples include phenyl and naphthyl.

"Heteroatom" generally is an atom that differs from those that typify a molecule. Thus, in a hydrocarbon, any atom not a carbon or a hydrogen is a heteroatom. Common biologically acceptable heteroatoms include oxygen, sulfur and nitrogen.

The term "heteroaryl" relates to an aryl group where one or more carbon atoms is replaced with a heteroatom. Examples are pyridyl, imidazolyl, pyrrolyl, thienyl, furyl, pyranyl, pyrimidinyl, pyridazinyl, indolyl, quinolyl, naphthyridinyl and isoxazoyl.

"Branched" means the structure contains one or more branches at one or more sites. A branch can be an R group as defined above or other side group.

The term "cycloalkyl" refers to a cyclic hydrocarbon. Some examples are cyclopropyl, cyclobutyl, cyclopentyl and cyclohexyl. May contain a bridge of varying length.

"Heterocycle" is a cycloalkyl where one or more carbon atoms are replaced with a heteroatom. Examples are pyrrolidinyl, piperidinyl and piperazinyl.

The term "heteroalkyl" is an alkyl where one or more carbon atoms are replaced with a heteroatom. An ether is a heteroalkyl.

By "substituted" is meant that the base organic radical has one or more substituent groups. Thus, an atom or group replaces another atom or group in a molecule. Representative substituents include a halogen, C1-C8 alkyl, —CN, alkoxyl, hydroxyl, sulfide, sulfate, sulfonamide, amine, amide, an alcohol, a keto group, C6-C18 aryl, a halogenated C1-C18 alkyl, a nitrite group or a nitrate group.

A "halogen" is, for example, chlorine, fluorine or bromine.

An "alkenyl" is a hydrocarbon containing one or more carbon-carbon double bonds. The hydrocarbon can be branched.

The term "ring" means one, one of a plurality of ring structures or a plurality of ring structures, where two or more of the plurality of rings can be fused, wherein the or one or more of the plurality of rings may be aromatic, contain a heteroatom, may be substituted or a combination thereof. The ring may be bicyclic or polycyclic. The ring may contain a bridge of varying length.

The term "side group" means an atom or molecule attached to another structure. Thus, a side group can be an R group defined above, an alkyl, an aryl, a cycloalkyl and so on.

The term "bridge" refers to a linker between two structures. For example, a non-cyclic hydrocarbon, such as an alkyl, alkenyl and the like, which can contain a heteroatom, can be substituted, can be branched or combinations thereof, can connect two cyclic hydrocarbons, such as aryl or cycloalkyl groups. The bridge also may be contained within a cyclic structure joining at least two atoms of the cyclic structure. The intramolecular bridge may contain 0, 1, 2, 3, 4 or more atoms. The intramolelcular bridge may be linear, branched and contain substitutions.

The compounds of interest contain functional groups that can be derivatized to form prodrugs to enhance bio-availability. Thus, the instant invention contemplates variants of the active compounds of interest that following administration, are metabolized to a bioactive form. Such bioactive drug precursors are also known as bioreversible carriers, latent drugs, drug delivery systems or prodrugs. ("Bioreversible Carriers in Drug Design" E. B. Roche, ed., Pergamon, N.Y., 1987; "Prodrugs as Novel Drug Delivery Systems", Higuchi & Stella, eds., American Chemical Society, DC, 1975)

Chemical modification of drugs is directed to address particular aspects of pharmacodynamics, such as how to enhance availability of a polar compound that must cross a lipid barrier, how to stabilize a compound normally susceptible to degradation in vivo and so on.

Other reasons to make prodrugs include bioactive drug toxicity, lack of specificity, instability, being metabolized at the absorption site, being absorbed too quickly, patient compliance, such as poor taste or pain at injection site, poor doctor acceptance or formulation problems as well.

A common modification is esterification, which is not limited to derivation of a carboxyl group. Chemistry exists for making such derivatives, for example, for amines, imines, sulfur containing substituents and amides as well.

In the case of esters, various substituents can be added thereto, including unbranched, cyclic or branched hydrocarbons that can be substituted, can contain one or more double or triple bonds, can contain ring structures, the hydrocarbon backbone can contain one or more heteroatoms, such as nitrogen, sulfur or oxygen, and so on.

When considering the R group for constructing the ester, another factor to consider is the susceptibility of enzymatic cleavage. Thus, steric charge and conformational factors can be determinative for bioavailability. For example, a branched alkyl group may provide steric hindrance for accessibility to the esterase active site, thereby slowing the rate of hydrolysis. That either may be less desirable, bioavailability is delayed, or desirable, bioavailability is prolonged.

In other circumstances, it is desirable to enhance aqueous solubility of a drug. Examples of substituents that achieve that goal include succinates, sulfates, hemisuccinates, phosphates, amino acids, acetates, amines and the like.

Nitrogens of amides, imides, carbonates, hydrantoins and the like can be derivatized. Suitable groups for reaction to the nitrogen include hydroxymethyl groups, or hydroxyalkyl groups in general, acyloxyalkyl groups and acyl groups.

Carbonyl groups also are sites for derivation. Examples of derivatives are Schiff bases, oxines, ketals, acetals, oxazolidines, thiazolidines and enol esters.

While the derivatives discussed above comprise covalent bonding of the substituent to the drug, a substituent may be attached to the drug in other ways, for example, hydrogen bonding, van der Waals forces, electrostatic forces, hydrophobic interactions and the like.

Yet another means of derivatization is to use substituents that are removed from a prodrug by a nonenzymatic mechanism. Examples include prodrugs that contain (2-oxo-1,3-dioxol-4-yl) methyl esters, Mannich bases, oxazolidines, esters with a basic side chain that catalyze intramolecular hydrolysis and esters or amides that undergo an intramolecular nucleophilic cyclization-elimination reaction. The cyclization mechanism is available for drugs containing phenols, alcohols and amines. "Prodrug Design" Testa & Mayer in "Encyclopedia of Pharmaceutical Technology," 2nd ed. V. 3, Swarbrick & Boylan, eds., Marcel Dekker, 2002.

Therefore, the instant invention contemplates any further modification of the compounds of interest practicing known synthesis methods to obtain compounds that once administered react or are acted on in vivo to yield a compound that modulates HM74 activity.

The term "equivalent amino acid residues" herein means the amino acids occupy substantially the same position within a protein sequence when two or more sequences are aligned for analysis. Preferred HM74 polypeptides of the instant invention have an amino acid sequence sufficiently identical to that of the wild-type HM74. By "wild-type" is meant the most prevalent form or allele present in a defined population, whether local or wider in scope. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least 96% identity with an HM74 activity are defined herein as sufficiently identical.

As used interchangeably herein, an "HM74 activity", "biological activity of HM74" or "functional activity of HM74", refers to an activity exerted by an HM74 protein, polypeptide or nucleic acid molecule on an HM74 expressing cell as determined in vivo or in vitro, according to standard techniques. An HM74 activity can be a direct activity, such as an association with or an enzymatic activity on a second protein or an indirect activity, such as a cellular signaling activity mediated by interaction of the HM74 with a second protein. In a preferred embodiment, an HM74 activity includes at least one or more of the following activities: (i) the ability to interact with proteins in the HM74 signaling pathway; (ii) the ability to interact with an HM74 ligand; (iii) the ability to alter the host cell when activated; (iv) activation on binding a molecule of the invention; and (v) the ability to interact with an intracellular target protein.

One aspect of the invention pertains to expressing HM74 in cells that demonstrate a response when HM74 is activated. As used herein, the term "nucleic acid molecule" is intended to include DNA molecules (e.g., cDNA or genomic DNA) and RNA molecules (e.g., mRNA) and analogs of DNA or RNA generated using nucleotide analogs. The nucleic acid molecule can be single-stranded or double-stranded, but preferably is double-stranded DNA.

An "isolated" nucleic acid molecule is one that is separated from other nucleic acid molecules present in the natural source of the nucleic acid. Preferably, an "isolated" nucleic acid is free of sequences that naturally flank the nucleic acid encoding HM74 (i.e., sequences located at the 5' and 3' ends of the nucleic acid) in the genomic DNA of the organism from that the nucleic acid is derived. The isolated HM74 nucleic acid molecule can contain less than about 5 kb, 4 kb, 3 kb, 2 kb, 1 kb, 0.5 kb or 0.1 kb of nucleotide sequences that naturally flank the open reading frame nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques or substantially free of chemical precursors or other chemicals when synthesized chemically.

A nucleic acid molecule of the instant invention, e.g., a nucleic acid molecule encoding HM74 can be isolated using standard molecular biology techniques and the sequence (Nomura et al., supra). Using all or a portion of the HM74 sequence, HM74 nucleic acid molecules can be isolated using standard hybridization and cloning techniques (e.g., as described in Sambrook et al., eds., Molecular Cloning: A Laboratory Manual, 2nd ed., Cold Spring Harbor Laboratory Press, Cold Spring Harbor, N.Y., 1989).

A nucleic acid molecule of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to HM74 nucleotide sequences can be prepared by standard synthetic techniques, e.g., using an automated DNA synthesizer.

Moreover, the nucleic acid molecule of the invention can comprise only portions of a nucleic acid sequence encoding HM74, for example, a fragment that encodes the extracellular domains and/or intracellular domains that yield a detectable intracellular event, when a ligand is bound thereto. Preferably that detectable intracellular event is one that is observed when HM74 is activated in a normal host cell.

A nucleic acid fragment encoding a "biologically active portion of HM74" can be prepared by isolating a portion of HM74 that encodes a polypeptide having an HM74 biological activity, expressing the encoded portion of HM74 protein (e.g., by recombinant expression in vitro) and assessing the activity of the encoded portion of HM74.

The invention further encompasses nucleic acid molecules that differ from the nucleotide sequence of the disclosed HM74 due to degeneracy of the genetic code and thus encode substantially the same HM74 protein as that previously disclosed.

It will be appreciated by those skilled in the art that DNA sequence polymorphisms that lead to changes in the amino acid sequences of HM74 may exist within a population (e.g., the human population). Such genetic polymorphism in the HM74 coding sequence may exist among individuals within a population due to natural allelic variation. An allele is one of a group of genes that occur alternatively at a given genetic locus. As used herein, the terms "gene" and "recombinant gene" refer to nucleic acid molecules comprising an open reading frame encoding an HM74 protein, preferably a mammalian HM74 protein. As used herein, the phrase "allelic variant" refers to a nucleotide sequence that occurs at an HM74 locus or to a polypeptide encoded by the nucleotide sequence. Alternative alleles can be identified by sequencing the gene of interest in a number of different individuals. That can be carried out readily by using hybridization probes to identify the same genetic locus in a variety of individuals. Any and all such nucleotide variations and resulting amino acid polymorphisms or variations in HM74 that are the result of natural allelic variation and that do not alter the functional activity of HM74 are intended to be within the scope of the invention.

Moreover, nucleic acid molecules encoding HM74 proteins from other species (HM74 homologues) with a nucleotide sequence that differs from that of a human HM74 but have substantially the same activity, are intended to be within the scope of the invention. Nucleic acid molecules corresponding to natural allelic variants and homologues of the HM74 cDNA of the invention can be isolated based on identity with the human HM74 nucleic acids disclosed herein using the human cDNA or a portion thereof, as a hybridization probe according to standard hybridization techniques under stringent hybridization conditions.

As used herein, the term "hybridizes under stringent conditions" is intended to describe conditions for hybridization and washing under which nucleotide sequences typically remain hybridized. Such stringent conditions are known to those skilled in the art and can be found in "Current Protocols in Molecular Biology", John Wiley & Sons, N.Y. (1989), 6.3.1-6.3.6. A preferred, non-limiting example of stringent hybridization conditions are hybridization in 6×sodium chloride/sodium citrate (SSC) at about 45° C., followed by one or more washes in 0.2×SSC, 0.1% SDS at 50-65° C. Preferably, an isolated nucleic acid molecule of the invention that hybridizes under stringent conditions to the sequence HM74 or the complement thereof corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the HM74 sequence that may exist in the population, the skilled artisan will further appreciate that changes can be introduced by mutation into the nucleotide sequence, thereby leading to changes in the amino acid sequence of the encoded HM74, without substantially altering the biological activity of the HM74 protein. Thus, one can make nucleotide substitutions leading to amino acid substitutions at "non-essential" amino acid residues. A "non-essential" amino acid residue is a residue that can be altered from the wild type sequence of HM74 without substantially altering the biological activity. An "essential" amino acid residue is one required for substantial biological activity. For example, amino acid residues that are not conserved or only semi-conserved among HM74 of various species may be non-essential for activity and thus would be likely targets of alteration. Alternatively, amino acid residues that are conserved among the HM74 proteins of various species may be essential for activity and thus would not be likely targets for alteration.

Accordingly, another aspect of the invention pertains to nucleic acid molecules encoding HM74 proteins that contain changes in amino acid residues that are not essential for activity. Such HM74 proteins differ from the known amino acid sequence yet retain biological activity. In one embodiment, the isolated nucleic acid molecule includes a nucleotide sequence encoding a protein that includes an amino acid sequence that is at least 96%, 97%, 98%, 99% or 100% identical to the known HM74 amino acid sequence.

An isolated nucleic acid molecule encoding an HM74 protein having a sequence that differs from that of the known HM74 can be created by introducing one or more nucleotide substitutions, additions or deletions into the nucleotide sequence of the known HM74 such that one or more amino acid substitutions, additions or deletions are introduced into the encoded protein.

Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains are defined in the art. The families include amino acids with basic side chains (e.g., lysine, arginine and histidine), acidic side chains (e.g., aspartic acid and glutamic acid), uncharged polar side chains (e.g., glycine, asparagine, glutamine, serine, threonine, tyrosine and cysteine), nonpolar side chains (e.g., alanine, valine, leucine, isoleucine, proline, phenylalanine, methionine and tryptophan), beta-branched side chains (e.g., threonine, valine and isoleucine) and aromatic side chains (e.g., tyrosine, phenylalanine, tryptophan and histidine). Thus, a predicted nonessential amino acid residue in HM74 preferably is replaced with another amino acid residue from the same side chain family. Alternatively, mutations can be introduced randomly along all or part of an HM74 coding sequence, such as by saturation mutagenesis, and the resultant mutants can be screened for HM74 biological activity to identify mutants that retain activity. Following mutagenesis, the encoded protein can be expressed recombinantly and the activity of the protein can be determined.

Examples of modified nucleotides that can be used to generate nucleic acids of interest include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, β-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, β-D-mannosylqueosine, 5-methoxycarboxymethyluracil, 5-methoxyuracil, 2-methylthio-N6-isopentenyladenine, uracil-5-oxyacetic acid, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl)uracil and 2,6-diaminopurine.

One way to impact HM74 function is to affect HM74 expression. Thus, transcription levels can be manipulated for lesser or greater levels of HM74 mRNA, which would in turn lead to lesser or greater levels of HM74 expression at the cell surface. One way to achieve such manipulation is by using regulatable promoters which can be introduced at the appropriate site in the genome, in proximity of the HM74 coding sequence by, for example, homologous recombination.

Accordingly, another aspect of the invention pertains to anti-HM74 antibodies. The term "antibody" as used herein refers to immunoglobulin molecules and immunologically active portions of immunoglobulin molecules, i.e., molecules that contain an antigen-binding site that specifically binds an antigen, such as HM74. A molecule that specifically binds to HM74 is a molecule that binds HM74, but does not substantially bind other molecules in a sample, e.g., a biological sample, that naturally contains HM74. Examples of immunologically active portions of immunoglobulin molecules include F(ab) and F(ab')2 fragments that can be generated by treating the antibody with an enzyme such as pepsin. The invention provides polyclonal and monoclonal antibodies that bind HM74. The term "monoclonal antibody" or "monoclonal antibody composition", as used herein, refers to a population of antibody molecules that contain only one species of an idiotype or a clone of an antigen-binding site capable of immunoreacting with a particular epitope of HM74. A monoclonal antibody composition thus typically displays a single binding affinity for a particular HM74 protein epitope.

Various other antigen-binding forms of antibodies can be made as known in the art, including fragments, chimeric antibodies, recombinant antibodies, humanized antibodies and the like.

Another aspect of the invention pertains to vectors, preferably expression vectors, containing a nucleic acid encoding HM74 (or a portion thereof). As used herein, the term "vector" refers to a nucleic acid molecule capable of transporting another nucleic acid linked thereto. One type of vector is a "plasmid" that refers to a circular double-stranded DNA loop into which additional DNA segments can be ligated. Another type of vector is a viral vector, wherein additional DNA segments can be ligated into a viral genome. Certain vectors are capable of autonomous replication in a host cell (e.g., bacterial vectors having a bacterial origin of replication and episomal mammalian vectors). Other vectors (e.g., non-episomal mammalian vectors) are integrated into the genome of a host cell on introduction into the host cell and thereby are replicated along with the host genome. Moreover, certain vectors, expression vectors, are capable of directing the expression of genes operably linked thereto. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), that serve equivalent functions.

The recombinant expression vectors of the invention comprise nucleic acid of the invention in a form suitable for expression of the nucleic acid in a host cell. That means the recombinant expression vectors include one or more regulatory sequences, selected on the basis of the host cells to be used for expression, which is linked operably to the nucleic acid to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology Vol. 185, Academic Press, San Diego, Calif. (1990). Regulatory sequences include those which direct constitutive expression of the nucleotide sequence in many types of host cells (e.g., tissue specific regulatory sequences). It will be appreciated by those skilled in the art that the design of the expression vector can depend on such factors as the choice of host cell to be transformed, the level of expression of protein desired etc. The expression vectors of the invention can be introduced into host cells to produce proteins or peptides encoded by nucleic acids as described herein (e.g., HM74, mutant forms of HM74, fusion proteins etc.).

The recombinant expression vectors of the invention can be designed for expression of HM74 in prokaryotic or eukaryotic cells, e.g., bacterial cells such as *E. coli*, insect cells (using baculovirus expression vectors), yeast cells or mammalian cells. Suitable host cells are discussed further in Goeddel, supra. Alternatively, the recombinant expression vector can be transcribed and translated in vitro, for example using T7 promoter regulatory sequences and T7 polymerase.

In another embodiment, the HM74 expression vector is a yeast expression vector. Examples of vectors for expression in yeast such as *S. cerevisiae* include pYepSecl (Baldari et al., EMBO J. (1987) 6:229-234), pMFa (Kurjan et al., Cell (1982) 30:933-943), pJRY88 (Schultz et al., Gene (1987) 54:113-123), pYES2 (Invitrogen Corporation, San Diego, Calif.) and pPicZ (Invitrogen Corp, San Diego, Calif.).

Alternatively, HM74 can be expressed in insect cells using baculovirus expression vectors. Baculovirus vectors available for expression of proteins in cultured insect cells (e.g., Sf 9 cells) include the pAc series (Smith et al., Mol. Cell. Biol. (1983) 3:2156-2165) and the pVL series (Lucklow et al., Virology (1989) 170:31-39).

In yet another embodiment, a nucleic acid of the invention is expressed in mammalian cells using a mammalian expression vector. Examples of mammalian expression vectors include pCDM8 (Seed, Nature (1987) 329:840) and pMT2PC (Kaufman et al., EMBO J. (1987) 6:187-195). When used in mammalian cells, the control functions of the expression vector often are provided by viral regulatory elements. For example, commonly used promoters are derived from polyoma, adenovirus 2, cytomegalovirus and simian virus 40. For other suitable expression systems for both prokaryotic and eukaryotic cells, see chapters 16 and 17 of Sambrook et al., supra.

For stable transformation of mammalian cells, it is known that, depending on the expression vector and transformation technique used, only a small fraction of cells may integrate the foreign DNA into the genome. To identify and to select the integrants, a gene that encodes a selectable marker (e.g., for resistance to antibiotics) generally is introduced into the host cells along with the gene of interest. Preferred selectable markers include those that confer resistance to drugs, such as G418, hygromycin and methotrexate. Nucleic acid encoding a selectable marker can be introduced into a host cell on the same vector as that encoding HM74 or can be introduced on a separate vector. Cells stably transfected with the introduced nucleic acid can be identified by drug selection (e.g., cells that have incorporated the selectable marker gene will survive, while the other cells die).

The compounds of interest that engage and activate HM74 are fused ring dihydropyrans, which includes oxydecalin-like compounds. Oxydecalin is another name for oxydecahydroraphthalene. Such dihydropyrans have the general structure:

The dihydropyrans and oxydecalins of interest can be made as taught in U.S. Pat. No. 6,399,653, WO 97/48691 and in von Roedern, Mol. Div. (1998) 3:253-256.

The oxydecalins of interest have the following structure:

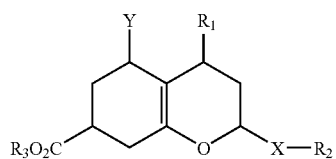

where X is O, $NR_2$ or S;

$R_1$ is a $C_1$-$C_{18}$ alkyl, which may be branched, may contain a heteroatom or may be substituted, or combinations thereof; a $C_1$-$C_{18}$ alkenyl, which may be branched, may contain a heteroatom or may be substituted, or combinations thereof; a $C_1$-$C_{18}$ alkynl, which may be branched, may contain a heteroatom or may be substituted, or combinations thereof; a $C_3$-$C_{18}$ aryl which may contain a side group, may contain a bridge, may contain a heteroatom or may be substituted, or combinations thereof; or a $C_5$-$C_{18}$ cycloalkyl which may contain a side group, may contain a bridge, may contain a heteroatom or may be substituted, or combinations thereof; or combinations thereof;

$R_2$ is an $R_1$ group; or $R_2$ can be a ($C_1$-$C_{10}$) alkyl-($C_3$-$C_{10}$) cycloalkyl, which may be branched, may contain a heteroatom or may be substituted, or combinations thereof; or X and $R_2$ may form a ring;

$R_3$ is H or $R_1$; and

Y is carbonyl, a Schiff base, an oxine, a ketal, an acetal, an oxazolidine, a thiazolidine or an enol ester.

The compounds of interest generally are agonists. Thus, a compound of interest could be developed as a drug candidate. A compound of interest also could be used to identify other molecules that modulate HM74 by, for example, competition assays.

Preferred compounds are those where when R2 is methyl, ethyl or cyclohexyl, R1 is not an n-alkyl or a C1-C4 branched alkyl; or when R1 is a C1-C4 alcohol or a C1-C4 branched alkyl which may be substituted with an acetyl group, R1 is not an n(—C1-C8) alkyl, a (C1-C4) branched alkyl or a thio substituted phenyl.

The term "alkyl" means a straight or branched chain hydrocarbon. Representative examples are methyl, ethyl, propyl, isopropyl, butyl, isobutyl, tert-butyl, sec-butyl, pentyl and hexyl. The hydrocarbon can contain one or more unsaturated triple bonds.

The term "alkoxy" means an alkyl group bound to an oxygen atom. Examples are methoxy, ethoxy, propoxy, butoxy and pentoxy.

"Aryl" is an aromatic hydrocarbon. Examples include phenyl and naphthyl.

"Heteroatom" generally is an atom that differs from those that typify a molecule. Thus, in a hydrocarbon, any atom not a carbon or a hydrogen is a heteroatom. Common biologically acceptable heteroatoms include oxygen, sulfur and nitrogen.

The term "heteroaryl" relates to an aryl group where one or more carbon atoms is replaced with a heteroatom. Examples are pyridyl, imidazolyl, pyrrolyl, thienyl, furyl, pyranyl, pyrimidinyl, pyridazinyl, indolyl, quinolyl, naphthyridinyl and isoxazoyl.

The term "cycloalkyl" refers to a cyclic hydrocarbon. Some examples are cyclopropyl, cyclobutyl, cyclopentyl and cyclohexyl.

"Heterocycle" is a cycloalkyl where one or more carbon atoms are replaced with a heteroatom. Examples are pyrrolidinyl, piperidinyl and piperazinyl.

The term "heteroalkyl" is an alkyl where one or more carbon atoms are replaced with a heteroatom. An ether is a heteroalkyl.

By "substituted" is meant that the base organic radical has one or more substituent groups. Thus, an atom or group replaces another atom or group in a molecule. Representative substituents include a halogen, C1-C8 alkyl, —CN, alkoxyl, hydroxyl, sulfide, sulfate, sulfonamide, amine, amide, an alcohol, a keto group, C6-C18 aryl, a halogenated C1-C18 alkyl, a nitrite group or a nitrate group.

A "halogen" is, for example, chlorine, fluorine or bromine.

An "alkenyl" is a hydrocarbon containing one or more carbon-carbon double bonds. The hydrocarbon can be branched.

The term "ring" means one or one of a plurality of ring structures, where two or more of the plurality of rings can be fused, wherein the or one or more of the plurality of rings may be aromatic, contain a heteroatom, may be substituted or a combination thereof. The ring may be bicyclic or polycyclic, and may contain a bridge.

The compounds of interest bind HM74 and activate HM74, but do not bind to HM74A.

The oxydecalins of interest can be synthesized as known in the art, U.S. Pat. No. 6,399,653.

Oxydecalin-like compounds of the invention can be incorporated into pharmaceutical compositions suitable for administration. Such compositions typically comprise the active ingredient and a pharmaceutically acceptable carrier. As used herein, the language "pharmaceutically acceptable carrier" is intended to include any and all solvents, dispersion media, coatings, antibacterial and antifungal agents, isotonic and absorption delaying agents and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds also can be incorporated into the compositions.

A pharmaceutical composition of the invention is formulated to be compatible with the intended route of administration. Examples of routes of administration include parenteral, e.g., intravenous, intradermal, subcutaneous, oral (e.g., inhalation), transdermal (topical), transmucosal and rectal administration. Solutions or suspensions used for parenteral, intradermal or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates and agents for the adjustment of tonicity such as sodium chloride or dextrose. pH can be adjusted with acids or bases, such as HCl or NaOH. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL® (BASF; Parsippany, N.J.) or phosphate-buffered saline (PBS). In all cases, the composition must be sterile and should be fluid to the extent that easy syringability exists. The composition must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyetheylene glycol and the like) and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols such as mannitol, sorbitol or sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze drying that yield a powder of the active ingredient plus any additional desired ingredient from a previously sterile-filtered solution thereof.

Oral compositions generally include an inert diluent or an edible carrier. The compositions can be enclosed in gelatin capsules or compressed into tablets. For the purpose of oral therapeutic administration, the active compound can be incorporated with excipients and used in the form of tablets, troches or capsules. Oral compositions also can be prepared using a fluid carrier to yield a syrup or liquid formulation, or for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate or orange flavoring.

For administration by inhalation, the compounds are delivered in the form of an aerosol spray from a pressurized container or dispenser that contains a suitable propellant, e.g., a gas such as carbon dioxide or a nebulizer.

Systemic administration also can be by transmucosal or transdermal means. For transmucosal or transdermal administration, penetrants appropriate to the barrier to be permeated are used in the formulation. Such penetrants generally are known in the art and include, for example, for transmucosal administration, detergents, bile salts and fusidic acid derivatives. Transmucosal administration can be accomplished through the use of nasal sprays or suppositories. For transdermal administration, the active compounds are formulated into ointments, salves, gels or creams as generally known in the art.

The compounds also can be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid.

Methods for preparation of such formulations will be apparent to those skilled in the art. The materials also can be obtained commercially from Alza Corporation and Nova Pharmaceuticals, Inc. Liposomal suspensions (including liposomes targeted to infected cells with monoclonal antibodies) also can be used as pharmaceutically acceptable carriers. Those can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. Depending on the type and severity of the disease, about 1 µg/kg to 15 mg/kg (e.g., 0.1 to 20 mg/kg) of active ingredient is an initial candidate dosage for administration to the patient, whether, for example, by one or more separate administrations or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of the therapy is monitored easily by conventional techniques and assays. An exemplary dosing regimen is disclosed in WO 94/04188. The specification for the dosage unit forms of the invention is dictated by and directly dependent on the unique characteristics of the active compound and the particular therapeutic effect to be achieved and the limitations inherent in the art of compounding such an active compound for the treatment of individuals.

The pharmaceutical compositions can be included in a container, pack or dispenser together with instructions for administration.

The HM74 modulators of interest can be used in screening assays and methods of treatment (e.g., therapeutic and prophylactic). The HM74 modulators of interest can be used to screen for other drugs or compounds that modulate HM74 activity or expression as well as to treat disorders characterized by inflammation. The modulators of interest may also find use in conditions resulting from insufficient or excessive production of HM74 protein or by production of HM74 protein forms that have decreased or aberrant activity compared to HM74 wild-type protein. The invention further pertains to novel HM74 modulators identified by the screening assays and uses thereof for treatments as described herein.

The invention provides a method (also referred to herein as a "screening assay") for identifying modulators, i.e., candidate or test compounds or agents (e.g., peptides, peptidomimetics, small molecules, antibodies or other drugs) that bind to HM74 and have a stimulatory or inhibitory effect on, for example, HM74 expression or HM74 activity.

In one embodiment, the invention provides assays for screening candidate or test compounds that bind to or modulate the activity of HM74. Thus, the screening assays can be used to identify other furosemide-like and oxydecalin-like compounds that modulate HM74. Such modulators also can be used in competition assays to identify other modulators such as HM74 antagonists.

In one embodiment, an assay is a cell-based assay in which a cell that expresses a membrane-bound form of HM74 on the cell surface is contacted with a test compound and the ability of the test compound to activate HM74 is determined. The cell, for example, can be a yeast cell or a cell of mammalian origin. Determining the ability of the test compound to activate HM74 can be accomplished, for example, by coupling the test compound with a radioisotope or enzymatic label such that binding of the test compound to HM74 can be determined by detecting the labeled compound in a complex with HM74, or where HM74 is located. For example, test compounds can be labeled with 125I, 35S, 14C or 3H, either directly or indirectly and the radioisotope detected by direct counting of radioemission or by scintillation counting. Alternatively, test compounds can be labeled enzymatically with, for example, horseradish peroxidase, alkaline phosphatase or luciferase and the enzymatic label detected by determination of conversion of an appropriate substrate to product. In a preferred embodiment, the assay comprises contacting a cell that expresses a membrane-bound form of HM74 on the cell surface with a known compound that binds HM74 along with a test compound and determining the ability of the test compound to compete with the known compound to interact with an HM74.

In another embodiment, an assay is a cell-based assay comprising contacting a cell expressing a membrane-bound form of HM74 on the cell surface with a test compound and determining the ability of the test compound to modulate (e.g., stimulate or inhibit) the activity of HM74. Determining the ability of the test compound to modulate the activity of HM74 can be accomplished, for example, by determining the ability of the test compound to activate or to inhibit HM74. That might be manifest when activated HM74 interacts with an intracellular or membrane target molecule associated with the signaling pathway. As used herein, a "target molecule" is a molecule with which HM74 binds or interacts in nature, for example, a molecule on the surface of a cell that expresses an HM74, a molecule on the surface of a second cell, a molecule in the extracellular milieu, a molecule associated with the internal surface of a cell membrane or a cytoplasmic molecule. An HM74 target molecule can be a non-HM74 molecule. In one embodiment, an HM74 target molecule is a component of a signal transduction pathway that facilitates transduction of an extracellular signal (e.g., a signal generated by binding of a compound to HM74) through the cell membrane and into the cell. The target, for example, can be a second intercellular protein that has catalytic activity or a protein that facilitates the association of downstream signaling molecules with HM74.

Determining the ability of the HM74 to bind to or to interact with an HM74 target molecule can be accomplished by one of the methods described above for determining direct binding. In a preferred embodiment, determining the ability of HM74 to bind to or to interact with an HM74 target molecule can be accomplished by determining the activity of the target molecule. For example, the activity of the target molecule can be determined by detecting induction of a cellular second messenger of the target (e.g., intracellular Ca2+, diacylglycerol, IP3 etc.), detecting catalytic/enzymatic activity of the target on an appropriate substrate, detecting the induction of a reporter gene (e.g., an HM74-responsive regulatory element operably linked to a nucleic acid encoding a detectable marker, e.g. luciferase) or detecting a cellular response, for example, cellular differentiation or cell proliferation.

In yet another embodiment, an assay of the instant invention is a cell-free assay comprising contacting HM74 with a test compound and determining the ability of the test compound to bind to the HM74. Binding of the test compound to HM74 can be determined either directly or indirectly as described above. In a preferred embodiment, the assay includes contacting HM74 with a known compound of the invention along with a test compound and determining the ability of the test compound to impact the HM74 activity of the known compound described herein. Determining the ability of the test compound to interact with HM74 comprises determining the ability of the test compound to preferentially bind to HM74 as compared to the binding of the known compound described herein.

In another embodiment, an assay is a cell-free assay comprising contacting HM74 with a test compound and determining the ability of the test compound to modulate (e.g., stimulate or inhibit) the activity of the HM74. Determining the ability of the test compound to modulate the activity of HM74 can be accomplished, for example, by determining the ability of the activated HM74 to bind to an HM74 target molecule by one of the methods described above for determining direct binding. In an alternative embodiment, determining the ability of the test compound to modulate the activity of HM74 can be accomplished by determining the ability of the HM74 to further modulate an HM74 target molecule. For example, the catalytic/enzymatic activity of the target molecule on an appropriate substrate can be determined as described previously.

In yet another embodiment, the cell-free assay comprises contacting HM74 with a known compound that binds HM74 with a test compound and determining the ability of the test compound to interact with an HM74, wherein determining the ability of the test compound to interact with an HM74 comprises determining the ability of HM74 preferentially to bind to or to modulate the activity of an HM74 target molecule.

Receptors can be activated by non-ligand molecules that necessarily do not inhibit ligand binding but cause structural changes in the receptor to enable G protein binding or, perhaps receptor aggregation, dimerization or clustering that can cause activation.

The cell-free assays of the instant invention are amenable to use of both the soluble form and the membrane-bound form of HM74. In the case of cell-free assays comprising the membrane-bound form of HM74, it may be desirable to utilize a solubilizing agent such that the membrane-bound form of HM74 is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton X-100, Triton X-114, Thesit®, isotridecylpoly(ethylene glycol ether)n, 3-[(3-cholamidopropyl)dimethylammino]-1-propane sulfonate (CHAPS), 3-[(3-cholamidopropyl)dimethylammino]-2-hydroxy-1-propane sulfonate (CHAPSO) or N-dodecyl=N,N-dimethyl-3-ammonio-1-propane sulfonate.

In another embodiment, HM74 is altered to be in a constant active state when expressed on a host cell. Altering HM74 can make the receptor active without having to bind ligand. One way to achieve an activated receptor is to alter HM74 to interact with G proteins without ligand binding. The alteration mimics the conformational changes of the receptor on ligand binding that enables the receptor to bind intracellular G proteins. One such approach is provided in WO 00/22129.

WO 00/22129 teaches particular amino acids in the region of TM6 and IC3 that yield constitutive activity. The methods for incorporating the particular amino acids into HM74 are known in the art, such as site-directed mutagenesis, subcloning and so on. The altered HM74 molecule then is expressed in a host cell to yield a constitutively active HM74.

The activated cell then is exposed to molecules suspected of being HM74 agonists, antagonists, inverse agonists and so on, molecules that alter HM74 activity. Those molecules that alter G protein activity are targeted for treating disorders associated with altered HM74 metabolism using methods known in pharmaceutic development.

In more than one embodiment of the above assay methods of the instant invention, it may be desirable to immobilize either HM74 or a target molecule thereof to facilitate separation of complexed from uncomplexed forms of one or both of the proteins, as well as to accommodate automation of the assay. Binding of a test compound to HM74 or interaction of HM74 with a target molecule in the presence and absence of a candidate compound, can be accomplished in any vessel suitable for containing the reactants. Examples of such vessels include microtitre plates, test tubes and microcentrifuge tubes. In one embodiment, a fusion protein can be provided that adds a domain that allows one or both of the proteins to be bound to a matrix. For example, glutathione-S-transferase/HM74 fusion proteins or glutathione-S-transferase/target fusion proteins can be adsorbed onto glutathione Sepharose® beads (Sigma Chemical, St. Louis, Mo.) or glutathione-derivatized microtitre plates. That complex then are combined with the test compound and either the non-adsorbed target protein or HM74 protein and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix and the level of HM74 binding or activity determined using standard techniques.

Other techniques for immobilizing proteins on matrices also can be used in the screening assays of the invention. For example, either HM74 or a target molecule thereof can be immobilized utilizing conjugation of biotin and streptavidin. Biotinylated HM74 or target molecules can be prepared from biotin-NHS (N-hydroxy-succinimide) using techniques well known in the art (e.g., biotinylation kit, Pierce Chemicals, Rockford, Ill.) and immobilized in the wells of streptavidin-coated 96-well plates (Pierce Chemicals). Alternatively, antibodies reactive with HM74 or target molecules but that do not interfere with binding of the HM74 protein to a target molecule can be derivatized to the wells of the plate and unbound target or HM74 trapped in the wells by antibody conjugation. Methods for detecting such complexes, in addition to those described above for the GST-immobilized complexes, include immunodetection of complexes using antibodies reactive with HM74 or target molecule, as well as enzyme-linked assays that rely on detecting an enzymatic activity associated with the HM74 or target molecule.

In another embodiment, modulators of HM74 expression are identified in a method in which a cell is contacted with a candidate compound and the expression of HM74 mRNA or protein in the cell is determined. The level of expression of HM74 mRNA or protein in the presence of the candidate compound is compared to the level of expression of HM74 mRNA or protein in the absence of the candidate compound. The candidate compound then can be identified as a modulator of HM74 expression based on that comparison. For example, when expression of HM74 mRNA or protein is greater (statistically significantly greater) in the presence of the candidate compound than in the absence thereof, the candidate compound is identified as a stimulator or agonist of HM74 mRNA or protein expression. Alternatively, when expression of HM74 mRNA or protein is less (statistically significantly less) in the presence of the candidate compound than in the absence thereof, the candidate compound is identified as an inhibitor or antagonist of HM74 mRNA or protein expression. If HM74 activity is reduced in the presence of ligand or agonist, or in a constitutive HM74, below baseline, the candidate compound is identified as an inverse agonist. The level of HM74 mRNA or protein expression in the cells can be determined by methods described herein for detecting HM74 mRNA or protein.

As large quantities of pure HM74 can be made, physical characterization of the conformation of areas of likely function can be ascertained for rational drug design. For example, the IC3 region of the molecule and EC domains are regions of particular interest. Once the shape and ionic configuration of a region are discerned, candidate drugs that interact with those regions can be configured and then tested in intact cells, animals and patients. Methods that would enable deriving such structure information include X-ray crystallography, NMR spectroscopy, molecular modeling and so on. The 3-D structure also can lead to identification of analogous conformational sites in other known proteins where known drugs that act at a particular site exist. Those drugs, or derivatives thereof, may find use with HM74.

The invention further pertains to novel agents identified by the above-described screening assays and uses thereof for treatments as described herein.

The instant invention provides for both prophylactic and therapeutic methods of treating a subject at risk of (or susceptible to) a disorder or having a disorder associated with aberrant HM74 expression or activity. Such disorders include, but are not limited to, for example, inflammatory disorders such as asthma, chronic obstructive pulmonary disease and rheumatoid arthritis.

In one aspect, the invention provides a method for preventing in a subject, a disease or condition associated with an aberrant HM74 expression or activity, by administering to the subject an agent that modulates HM74 expression or at least one HM74 activity. Subjects at risk for a disease that is caused by or contributed to by aberrant HM74 expression or activity can be identified by, for example, any or a combination of diagnostic or prognostic assays as described herein. Administration of a prophylactic agent can occur prior to the manifestation of symptoms characteristic of the HM74 aberrancy, such that a disease or disorder is prevented or, alternatively, delayed in progression. Depending on the type of HM74 aberrancy, for example, an HM74 agonist or HM74 antagonist agent can be used for treating the subject. The appropriate agent can be determined based on screening assays described herein.

Another aspect of the invention pertains to methods of modulating HM74 expression or activity for therapeutic purposes. The modulatory method of the invention involves contacting a cell with an agent that modulates one or more of the activities of HM74 associated with the cell. An agent that modulates HM74 activity can be an agent as described herein, such as a furosemide or oxydecalin, nucleic acid or a protein, a naturally-occurring cognate ligand of an HM74 protein, a peptide, an HM74 peptidomimetic or other small molecule. In one embodiment, the agent stimulates one or more of the biological activities of HM74. In another embodiment, the agent inhibits one or more of the biological activities of HM74 protein. Examples of such inhibitory agents include anti-HM74 antibodies. The modulatory methods can be performed in vitro (e.g., by culturing the cell with the agent) or, alternatively, in vivo (e.g., by administering the agent to a subject). As such, the instant invention provides methods of treating an individual afflicted with a disease or disorder characterized by aberrant expression or activity of an HM74. In one embodiment, the method involves administering an agent (e.g., an agent identified by a screening assay described herein) or combination of agents that modulates (e.g., upregulates or downregulates) HM74 expression or activity.

Stimulation of HM74 activity is desirable in situations in which HM74 is downregulated abnormally and/or in which increased HM74 activity is likely to have a beneficial effect. Conversely, inhibition of HM74 activity is desirable in situations in which HM74 is upregulated abnormally and/or in which decreased HM74 activity is likely to have a beneficial effect.

The invention is illustrated further by the following examples which should not be construed as limiting. The contents of all references, patents and published patent applications cited throughout the application hereby are incorporated by reference.

EXAMPLE 1

Generation of Mammalian Cells Expressing HM74

The cDNA encoding hHM74 is cloned into an expression vector and transfected into mammalian cells, such as CHO cells or 293 cells.

To generate mammalian cells overexpressing HM74, mammalian cells are plated in a six-well 35 mm tissue culture plate (3×105 mammalian cells per well (ATCC Catalog No. CRL-1573)) in 2 ml of DMEM media (Gibco/BRL, Catalog No. 11765-054) in the presence of 10% fetal bovine serum (Gibco/BRL Catalog No. 1600-044).

The cells then are incubated at 37° C. in a CO2 incubator until the cells are 50-80% confluent. The cloned cDNA nucleic acid sequence of HM74 is inserted in a pcDNA 3.1 cloning vector (Invitrogen, Catalog No. V790-20). Two µg of the DNA are diluted into 100 µl of serum-free F12 Ham's medium. Separately, 25 µl of Lipofectamine Reagent (Life Technologies, Catalog No. 18324-020) is diluted into 100 µl of serum-free F12 Ham's medium. The DNA solution and the Lipofectamine solution then are mixed gently and incubated at room temperature for 45 minutes to allow for the formation of DNA-lipid complexes.

The cells are rinsed once with 2 ml of serum-free F12 Ham's medium. For each transfection (six transfections in a six-well plate), 0.8 ml of serum-free F12 Ham's medium are added to the solution containing the DNA-lipid complexes (0.2 ml total volume) and mixed gently. The resulting mixture (hereinafter the "transfection mixture") then is overlaid (0.8 ml+0.2 ml) onto the rinsed cells. No antibacterial reagents are added. The cells then are incubated with the lipid-DNA complexes for 16 hours at 37° C. in a CO2 incubator to allow for transfection.

After the completion of the incubation period, 1 ml of F12 Ham's medium containing 10% fetal bovine serum is overlaid onto the cells without first removing the transfection mixture. At 18 hours after transfection, the media overlaying the cells is aspirated. Cells then are washed with PBS, pH 2-4 (Gibco/BRL Catalog No. 10010-023) and the PBS is replaced with F12 Ham's medium containing 5% serum ("selective media"). At 72 hours after transfection, the cells are diluted ten-fold into the selective medium containing the antibacterial agent genetecin at 400 µg/ml (Life Technologies, Catalog No. 11811).

EXAMPLE 2

Agonist Assay

To screen for agonists of human HM74, HM74 can be coupled artificially to a $G_q$ mechanism. Activation of the $G_q$ mechanism stimulates the release of $Ca^{2+}$ from sarcoplasmic reticulum vesicles within the cell. The $Ca^{2+}$ is released into the cytoplasm where it can be detected using $Ca^{2+}$ chelating dyes. A Fluorometric Imaging Plate Reader or FLIPR® apparatus (Molecular Devices) is used to monitor any resulting changes in fluorescence. The activity of an agonist is reflected by any increase in fluorescence.

CHO-K1 cells expressing HM74 are pre-engineered to express an indiscriminate form of Gq protein (Gα16). To prepare such cells, Gα16-coupled CHO cells are obtained commercially (Molecular Devices LIVEWARETM cells, Catalog No. RD-HGA16) and the protocol in Example 1, followed to facilitate expression of HM74 in those cells.

The cells are maintained in log phase of growth at 37° C. and 5% CO2 in F12 Ham's media (Gibco/BRL, Catalog No. 11765-054) containing 10% fetal bovine serum, 100 IU/ml penicillin (Gibco/BRL, Catalog No. 15140-148), 100 μg/ml streptomycin (Catalog No. 15140-148, Gibco/BRL), 400 μg/ml geneticin (G418) (Gibco/BRL, Catalog No. 10131-035) and 200 μg/ml zeocin (Invitrogen, Catalog No. R250-05). One day prior to an assay, 12,500 cells/well of the CHO-K1 cells are plated onto 384-well clear-bottomed assay plates with a well volume of 50 μl (Greiner/Marsh, Catalog No. N58102) using a 96/384 Multidrop device (Labsystems, Type 832). The cells are incubated at 37° C. in a humidified 5% CO2 incubator (Forma Scientific CO2 water-jacketed incubator Model 3110).

The following stock solutions are prepared: a 1 M stock solution of Hepes (pH 7.5) (Gibco/BRL, Catalog No. 15630-080); a 250 mM stock solution of probenicid (Sigma, Catalog No. P8761) made in 1 N NaOH; and a 1 mM stock solution of Fluo 4-AM Dye (Molecular Probes, Catalog No. Fl 4202) made in DMSO (Sigma D2650). Reaction buffer is prepared with 1000 ml Hank's balanced salt solution (Fisher/Mediatech, Catalog No. MT21023), 20 ml of the 1 M Hepes stock solution and 10 ml of the 250 mM probenicid stock solution. To prepare the loading buffer, 1.6 ml of the 1 mM Fluo 4-AM Dye stock solution is mixed with 0.32 ml of pluronic acid (Molecular Probes, Catalog No. P6866) and then mixed with 400 ml of the above reaction buffer and 4 ml of fetal bovine serum.

One hour prior to the assay, 50 μl of freshly-prepared loading buffer is added to each well of the 384-well plate using a 96/384 Multidrop device. The cells are incubated at 37° C. in a humidified incubator to maximize dye uptake. Immediately prior to the assay, the cells are washed 2 times with 90 μl of reaction buffer using a 384 EMBLA Cell Washer (Skatron; Model No. 12386) with the aspiration head set at least 10 mm above the plate bottom, leaving 45 μl of buffer per well.

The CCD camera (Princeton Instruments) of the FLIPR® II (Molecular Devices) instrument is set at an f-stop of 2.0 and an exposure of 0.4 seconds. The camera is used to monitor the cell plates for accuracy of dye loading.

A compound library containing possible oxydecalin-like compounds is tested at a concentration of about 10 μM each in physiological salt buffer per well. Changes in fluorescence are measured for 10 seconds prior to compound addition. After the addition of the compound, fluorescence is measured every second for the first minute followed by exposures taken every six seconds for a total experimental analysis time of three minutes. Five μl aliquots of the 100 μM stock compound are added after the tenth scan, giving a final compound concentration on the cells of 10 μM. The maximum fluorescence changes for the first 80 scans are recorded as a measure of agonist activity and compared to the maximum fluorescence change induced by 10 μM ATP (Sigma A9062).

A number of oxydecalin compounds were found to activate HM74.

EXAMPLE 3

Antagonist Assay

To screen for antagonists of human HM74, HM74 can be coupled artificially to a $G_q$ mechanism. As in Example 2, a FLIPR® apparatus is used to monitor any resulting changes in fluorescence. The activity of an antagonist is reflected by any decrease in fluorescence.

CHO-K1 cells expressing HM74 are pre-engineered to express an indiscriminate form of Gq protein (Gα16), as described in Example 2. The cells are maintained in log phase of growth at 37° C. and 5% CO2 in F12 Ham's medium (Gibco/BRL, Catalog No. 11765-054) containing 10% fetal bovine serum, 100 IU/ml penicillin (Gibco/BRL, Catalog No. 15140-148), 100 μg/ml streptomycin (Catalog No. 15140-148, Gibco/BRL), 400 μg/ml geneticin (G418) (Gibco/BRL, Catalog No. 10131-035) and 200 μg/ml zeocin (Invitrogen, Catalog No. R250-05). One day prior to the assay, 12,500 cells/well of the CHO-K1 cells are plated onto 384-well black/clear bottomed assay plates with a well volume of 50 μl (Greiner/Marsh, Catalog No. N58102) using a 96/384 Multidrop device. The cells are allowed to incubate at 37° C. in humidified 5% CO2.

The following stock solutions are prepared: a 1 M stock solution of Hepes (pH 7.5) (Gibco/BRL, Catalog No. 15630-080); a 250 mM stock solution of probenicid (Sigma, Catalog No. P8761) made in 1 N NaOH; a 1 mM stock solution of Fluo 4-AM Dye (Molecular Probes, Catalog No. F 14202) made in DMSO (Sigma D2650); and a stock solution of ligand or antagonist. Reaction buffer is prepared with 1000 ml Hank's balanced salt solution (Fisher/Mediatech, Catalog No. MT21023), 20 ml of the 1 M Hepes stock solution, 10 ml of the 250 mM probenicid stock solution and 1 mM CaCl2. To prepare the loading buffer, 80 μl of the 1 mM Fluo 4-AM Dye stock solution is mixed with 16 μl of pluronic acid (Molecular Probes, Catalog No. P6866) and then mixed with 20 ml of the above reaction buffer and 0.2 ml of fetal bovine serum.

Thirty minutes prior to the assay, 30 μl of freshly-prepared loading buffer is added to each well of the 384-well plate using a 96/384 Multidrop device. The cells are incubated at 37° C. in a humidified CO2 incubator to maximize dye uptake. Immediately prior to the assay, the cells are washed 3 times with 100 μl of reaction buffer using a 384 EMBLA Cell Washer with the aspiration head set at least 40 mm above the plate bottom, leaving 45 μl of buffer per well.

Five μl of the 100 μM stock antagonist compound are added to the cells using a Platemate-384 pipetor (Matrix). The compound concentration during the incubation step is approximately 10 μM. The cells are placed on the FLIPR® II and plate fluorescence is measured every second for the first minute followed by exposures taken every six seconds for a total experimental analysis time of three minutes. Antagonist or ligand (10 μM) is added after the tenth scan. After each addition, the 384 tips are washed 10 times with 20 μl of 0.01% DMSO in water.

The HM74 cells either can be exposed to an identified agonist or not prior to testing with candidate antagonists.

EXAMPLE 4

Receptor Binding Assay

To prepare membrane fractions containing HM74, CHO cell lines expressing HM74 are harvested by incubation in phosphate-buffered saline (10 ml) containing 1 mM EDTA.

The cells are washed further 3 times in phosphate-buffered saline containing 1 mM EDTA (10 ml) prior to resuspension in 5 ml of Buffer A (50 mM Tris-HCl (pH 7.8) (Sigma T6791), 5 mM MgCl2 (Sigma M8266) and 1 mM EGTA (Sigma 0396).

The cells then are disrupted with a tissue homogenizer (Polytron, Kinemetica, Model PT 10/35) for 1 minute. The resulting homogenate is centrifuged in a Sorvall Instruments RC3B refrigerated centrifuge at 49,000×g at 4° C. for 20 minutes. The resulting pellet is resuspended in 25 ml of Buffer A and the centrifugation step is repeated three times. Following the final centrifugation, the pellet again is resuspended in 5 ml of Buffer A, aliquoted and stored at −70° C.

A receptor binding assay using the membrane fraction and a radiolabeled agonist of interest as a tracer is performed. The assay is performed in a 96-well plate (Beckman Instruments). The binding reaction consists of 18 µg of the CHO cell preparation in the presence of radioactive agonist (0.01 nM-25 nM) in a final volume of 0.2 ml of Buffer A containing 0.1% bovine serum albumin (Sigma, Catalog No. 34287) (see Im et al., J. Biol. Chem. (2000) 275(19): 14281-14286). The reaction is incubated for 1 hour at room temperature. The reaction is terminated by filtration through Whatman GF/C filters on a multichannel harvester (Brandell) that is pretreated with 0.3% polyethyleneimine (Sigma, Catalog No. P3143) and 0.1% bovine serum albumin (BSA) for 1 hour. The mixture is applied to the filter and incubated for one hour. The filters are washed 6 times with 1 ml of ice cold 50 mM Tris-HCl, pH 7.6. Specific binding is calculated based on the difference between total binding and non-specific binding (background) for each tracer concentration by measuring the radioactivity. Eight to 16 concentration data points are obtained to determine the binding of agonist to the receptor achieved in an equilibrium state between the agonist and receptor (equilibrium binding parameters). In a competitive assay, a test compound is added to the mixture to compete for the binding of radioactive agonist on the receptor (competition binding values). Inhibition curves are prepared to determine the concentration required to achieve a 50% inhibition of binding (IC50).

EXAMPLE 5

Small Molecule Agonists

A series of oxydecalin-like molecules were exposed to cells expressing HM74 as described above. Target molecules were labeled to determine whether binding to HM74 occurred. Binding was detected by determining the degree of labeling of the cells following washing. Binding also was ascertained by isolating HM74 by 2-D gel electrophoresis and determining the degree of labeling associated with that protein. Following that binding assessment, or independent of that binding assessment, the ability of a candidate agonist to activate HM74 was determined. The FLIPR assay was used to assess intracellular calcium mobilization on binding of target molecule to HM74. Thus, oxydecalin molecules that caused calcium mobilization were identified.

The invention now having been described, the artisan will know that various changes and modifications can be make to the teachings herein without departing from the spirit and scope of the invention taught herein.

All references cited herein are incorporated by reference in entirety herein.

What is claimed is:

1. A method for identifying an agonist of HM74 comprising, contacting a potential agonist with a cell expressing HM74 and determining whether in the presence of said potential agonist the signaling activity of HM74 is increased relative to the activity of HM74 in the absence of said potential agonist, wherein said potential agonist has the structure:

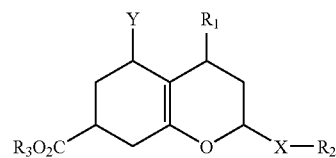

where X is O, NR$_2$ or S;

R$_1$ is a C$_1$-C$_{18}$ alkyl, which may be branched, may contain a heteroatom or may be substituted, or combinations thereof; a C$_1$-C$_{18}$ alkenyl, which may be branched, may contain a heteroatom or may be substituted, or combinations thereof; a C$_1$-C$_{18}$ alkynl, which may be branched, may contain a heteroatom or may be substituted, or combinations thereof: a C$_3$-C$_{18}$ aryl which may contain a side group, may contain a bridge, may contain a heteroatom or may be substituted, or combinations thereof; or a C$_5$-C$_{18}$ cycloalkyl which may contain a side group, may contain a bridge, may contain a heteroatom or may be substituted, or combinations thereof; or combinations thereof;

R2 is an R1 group, a (C1-C10) alkyl-(C3-C10) cycloalkyl, which may be branched, may contain a heteroatom or may be substituted, or combinations thereof; or X and R2 may form a ring;

R3 is H or R1; and

Y is carbonyl, a Schiff base, an oxine, a ketal, an acetal, an oxazolidine, a thiazolidine or an enol ester.

2. A method for identifying an inverse agonist of HM74 comprising, contacting a potential inverse agonist with a cell expressing HM74 and determining whether in the presence of said potential inverse agonist, the activity of HM74 is decreased relative to the activity of HM74 in the absence of said potential inverse agonist, and is decreased in the presence of an agonist, wherein said potential inverse agonist has the structure:

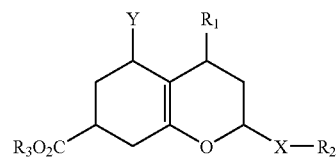

where X is O, NR$_2$ or S;

R$_1$ is a C$_1$-C$_{18}$ alkyl, which may be branched, may contain a heteroatom or may be substituted, or combinations thereof; a C$_1$-C$_{18}$ alkenyl, which may be branched, may contain a heteroatom or may be substituted, or combinations thereof; a C$_1$-C$_{18}$ alkynl, which may be branched, may contain a heteroatom or may be substituted, or combinations thereof; a C$_3$-C$_{18}$ aryl which may contain a side group, may contain a bridge, may contain a heteroatom or may be substituted, or combinations thereof; or a C$_5$-C$_{18}$ cycloalkyl which may contain a side group, may contain a bridge, may contain a heteroatom or may be substituted, or combinations thereof; or combinations thereof;

$R_2$ is an $R_1$ group, a $(C_1\text{-}C_{10})$ alkyl-$(C_3\text{-}C_{10})$ cycloalkyl, which may be branched, may contain a heteroatom or may be substituted, or combinations thereof; or X and $R_2$ may form a ring;

$R_3$ is an H or $R_1$; and

Y is carbonyl or oxygen bound to a Schiff base, an oxine, a ketal, an acetal, an oxazolidine, a thiazolidine or an enol ester.

3. A method for identifying an antagonist of HM74 comprising, contacting a potential antagonist with a cell expressing HM74 and determining whether in the presence of said potential antagonist the signaling activity of HM74 is decreased relative to the activity of HM74 in the presence of an agonist, wherein said potential antagonist has the structure:

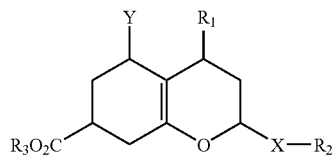

where X is O, $NR_2$ or S;

$R_1$ is a $C_1\text{-}C_{18}$ alkyl, which may be branched, may contain a heteroatom or may be substituted, or combinations thereof; a $C_1\text{-}C_{18}$ alkenyl, which may be branched, may contain a heteroatom or may be substituted, or combinations thereof; a $C_1\text{-}C_{18}$ alkynl, which may be branched, may contain a heteroatom or may be substituted, or combinations thereof; a $C_3\text{-}C_{18}$ aryl which may contain a side group, may contain a bridge, may contain a heteroatom or may be substituted, or combinations thereof; or a $C_5\text{-}C_8$ cycloalkyl which may contain a side group, may contain a bridge, may contain a heteroatom or may be substituted, or combinations thereof; or combinations thereof;

$R_2$ is an $R_1$ group, a $(C_1\text{-}C_{10})$ alkyl-$(C_3\text{-}C_{10})$ cycloalkyl, which may be branched, may contain a heteroatom or may be substituted, or combinations thereof; or X and $R_2$ may form a ring;

$R_3$ is H or $R_1$; and

Y is carbonyl, a Schiff base, an oxine, a ketal, an acetal, an oxazolidine, a thiazolidine or an enol ester.

* * * * *

UNITED STATES PATENT AND TRADEMARK OFFICE
CERTIFICATE OF CORRECTION

PATENT NO. : 7,264,937 B2  Page 1 of 1
APPLICATION NO. : 11/057263
DATED : September 4, 2007
INVENTOR(S) : Minnich et al.

It is certified that error appears in the above-identified patent and that said Letters Patent is hereby corrected as shown below:

Column 24, line 20, replace "alkynl" with --alkynyl--;

line 59, replace "alkynl" with --alkynyl--;

Column 26, line 6, replace "alkynl" with --alkynyl--.

Signed and Sealed this

Sixth Day of May, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,264,937 B2 | Page 1 of 1 |
| APPLICATION NO. | : 11/057263 | |
| DATED | : September 4, 2007 | |
| INVENTOR(S) | : Anne Minnich et al. | |

It is certified that error appears in the above-identified patent and that said Letters Patent is hereby corrected as shown below:

In column 24, line 22, in claim 1, delete "thereof:" and insert -- thereof; --, therefor.

In column 24, line 28, in claim 1, after "thereof;" delete "or combinations thereof;".

In column 24, line 67, in claim 2, after "thereof;" delete "or combinations thereof;".

In column 26, line 11, in claim 3, delete "$C_5$-$C_8$" and insert -- $C_5$-$C_{18}$ --, therefor.

In column 26, line 14, in claim 3, after "thereof;" delete "or combinations thereof;".

Signed and Sealed this
Twelfth Day of April, 2011

David J. Kappos
*Director of the United States Patent and Trademark Office*